United States Patent
Radaelli et al.

(10) Patent No.: US 9,771,317 B2
(45) Date of Patent: Sep. 26, 2017

(54) PROCESS FOR PREPARING LACOSAMIDE AND RELATED COMPOUNDS

(71) Applicants: CAMBREX KARLSKOGA AB, Karlskoga (SE); CAMBREX PROFARMACO MILANO, Paullo (IT)

(72) Inventors: Stefano Radaelli, Monza (IT); Giuseppe Zurlo, Paullo (IT); Lars Eklund, Umeå (SE); Margus Eek, Viimsi vald (EE); Ants Maasalu, Tallinn (EE); Malle Schmidt, Tallinn (EE)

(73) Assignees: Cambrex Karlskoga AB, Karlskoga (SE); Cambrex Profarmaco Milano, Paullo (MI) (IT)

(*) Notice: Subject to any disclaimer, the term of this patent is extended or adjusted under 35 U.S.C. 154(b) by 91 days.

(21) Appl. No.: 14/439,916

(22) PCT Filed: Nov. 1, 2013

(86) PCT No.: PCT/GB2013/052874
§ 371 (c)(1),
(2) Date: Apr. 30, 2015

(87) PCT Pub. No.: WO2014/068333
PCT Pub. Date: May 8, 2014

(65) Prior Publication Data
US 2015/0299105 A1 Oct. 22, 2015

(30) Foreign Application Priority Data
Nov. 1, 2012 (GB) .................... 1219627.5

(51) Int. Cl.
| | |
|---|---|
| C07C 231/12 | (2006.01) |
| C07C 237/06 | (2006.01) |
| C07C 231/24 | (2006.01) |
| C07C 233/47 | (2006.01) |
| C07C 231/22 | (2006.01) |
| C07C 233/46 | (2006.01) |
| C07C 247/12 | (2006.01) |

(52) U.S. Cl.
CPC .......... *C07C 231/12* (2013.01); *C07C 231/22* (2013.01); *C07C 231/24* (2013.01); *C07C 233/46* (2013.01); *C07C 233/47* (2013.01); *C07C 237/06* (2013.01); *C07C 247/12* (2013.01); *C07B 2200/13* (2013.01)

(58) Field of Classification Search
CPC ... C07C 231/12; C07C 237/06; C07C 231/24; C07C 233/47

USPC .......................................................... 562/512
See application file for complete search history.

(56) References Cited

U.S. PATENT DOCUMENTS

| | | | |
|---|---|---|---|
| 5,378,729 | A | 1/1995 | Kohn et al. |
| 5,773,475 | A | 6/1998 | Kohn |
| 6,048,899 | A | 4/2000 | Kohn et al. |
| 2008/0027137 | A1 | 1/2008 | Riedner et al. |
| 2011/0263899 | A1 | 10/2011 | Bouvy et al. |
| 2013/0085304 | A1 | 4/2013 | Madhra et al. |

FOREIGN PATENT DOCUMENTS

| | | |
|---|---|---|
| CN | 101591300 A | 12/2009 |
| DE | 1028557 B | 3/1957 |
| EP | 1642889 A1 | 5/2006 |
| EP | 2067765 A2 | 10/2009 |
| WO | 2010052011 A1 | 5/2010 |
| WO | 2011061610 A2 | 5/2011 |
| WO | 2011092559 A1 | 8/2011 |
| WO | 2011158194 A1 | 12/2011 |
| WO | 2012041986 A1 | 4/2012 |
| WO | 2012069855 A1 | 5/2012 |

OTHER PUBLICATIONS

May 5, 2015—(PCT) International Preliminary Report on Patentability & Written Opinion—App. No. PCT/GB2013/052874.
International Search Report dated May 14, 2014; ISA/EP.

*Primary Examiner* — Shaojia Anna Jiang
*Assistant Examiner* — Everett White
(74) *Attorney, Agent, or Firm* — Banner & Witcoff, Ltd.

(57) ABSTRACT

There is provided a process for the preparation of Lacosamide in a particular polymorphic form, which process involves the isolation of a salt of formula I: according to the methods defined in the application.

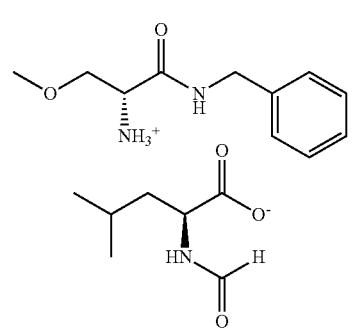

24 Claims, No Drawings

PROCESS FOR PREPARING LACOSAMIDE AND RELATED COMPOUNDS

The present invention relates to an improved process for the preparation of Lacosamide in pure polymorphic form which involves the isolation of a novel salt.

Lacosamide is an anti-convulsive drug, useful for the adjunctive treatment of partial onset seizures and diabetic neuropathic pain.

Processes for preparing Lacosamide have been disclosed in international patent application WO 2012/041986, as well as in earlier documents including international patent application WO 2010/052011, U.S. patent documents U.S. Pat. Nos. 5,378,729, 5,773,475, 6,048,899 and U.S. Ser. No. 2008/0027137, European patent documents EP 1 642 889 and EP 2 067 765 and Chinese patent document CN 101591300.

Processes for preparing Lacosamide have been disclosed in international patent applications WO 2012/069855 and WO 2011/158194 via selective enzymatic acylation. However, the yield and selectivity of the processes described in these applications are relatively low, thus reducing the economic viability of use of these processes in the manufacture of pharmaceuticals.

Earlier processes usually employed D-serine as a starting material, which is expensive and therefore has a drawback. More recently international patent application WO 2010/052011 discloses a resolution of Lacosamide (i.e. the amide), which resolution step is performed by the use of certain chiral chromatographic techniques. The undesired amide enantiomer is then racemised in a separate step, and the resolution to separate Lacosamide from the undesired amide enantiomer is repeated.

Resolution of 2-amino-N-benzyl-3-methoxypropanamide by diastereomeric salt formation with mandelic acid, malic acid, O,O'-dibenzoyltartaric acid, N-acetyl-L-alanine and N-acetyl-D-leucine are mentioned in WO 2010/052011.

Resolution of 2-amino-N-benzyl-3-methoxypropanamide by diastereomeric salt formation with mandelic acid, 2-chloro-mandelic acid, 3-chloro-mandelic acid, 4-chloro-mandelic acid, O,O'-dibenzoyltartaric acid, tartaric acid, and camphorsulfonic acid are disclosed in WO 2011/092559.

Furthermore, many documents describe sequences of reactions to obtain racemic N-benzyl-2-amino-3-methoxy-propanamide and N-benzyl-2-benzylamino-3-methoxypro-panamide, such as WO 2010/052011 and WO 2012/069855. However some of the steps involved in these sequences of reactions require relatively toxic reagents, such as sodium azide, result in low yields or generate a large quantity of waste material.

There is a need for alternative and/or improved reactions for the formation of single amide enantiomers (e.g. Lacosamide), which are more selective and/or advantageous in terms of being obtainable in higher yields, utilising fewer (or less cumbersome) synthetic steps, and involving cheaper and/or less toxic starting materials. This is important for process chemistry, in particular when scaling up.

The listing or discussion of an apparently prior-published document in this specification should not necessarily be taken as an acknowledgement that the document is part of the state of the art or common general knowledge.

In a first aspect of the invention, there is provided a process for the isolation of a salt of formula I:

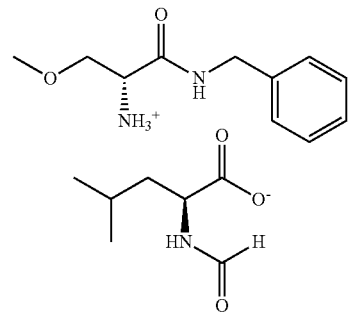

which process comprises precipitation of the salt of formula I from a mixture of N-formyl-L-leucine, a compound of formula II,

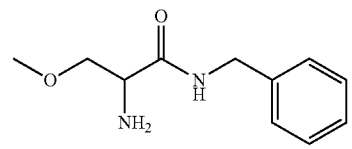

and a solvent for the compound of formula II;
which process is hereinafter referred to as "the process of the invention".

When used herein, the term "isolating" means preparing in solid form, whether or not separated from some or all of the liquid(s) (e.g. the solvent) present in the reaction mixture. In particular embodiments of the invention, however, the salt of formula I is isolated as a dry solid (i.e. separated, e.g. by filtration, from the reaction mixture in which it is formed).

The salt of formula I is novel. Thus, according to a second aspect of the invention there is provided the salt of formula I, or a solvate thereof.

The compound of formula II may be racemic (i.e. a 1:1 mixture of the two possible configurations at the chiral carbon atom that bears the —NH$_2$ group). Alternatively, the compound of formula II may be enriched with either the (S)- or (R)-enantiomer, provided that it is not enriched with the (R)-enantiomer to provide an enantiomeric excess (e.e.) of over 85%. In particular embodiments of the invention, however, the compound of formula II is racemic.

The reaction of the compound of formula II with a chiral amino acid derivative promotes the isolation of a diastereomeric salt including essentially only one of the two enantiomers (the (R)-enantiomer) of the compound of formula II. Thus the salt isolation step is diastereoselective.

The N-formyl-L-leucine that is used contains a greater amount of the acylated L-form of the amino acid, i.e.:

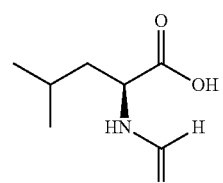

N-formyl-L-leucine compared to the D-form of that N-formyl amino acid. In particular, the N-formyl-L-leucine contains N-formyl-L-leucine in an enantiomeric excess of greater than 60%, more particularly greater than 70%, such as greater than 80%, or especially greater than 90% relative to N-formyl-D-leucine. Correspondingly, in particular embodiments, the N-formyl-L-leucine contains less than 40%, more particularly less than 30%, such as less than 20%, or especially less than 10% of N-formyl-D-leucine. Most particularly, the enantiomeric excess of the N-formyl-L-leucine is close to 100% (i.e. greater than 95%, for example greater than 99%), with a negligible amount of the acylated D-form.

The (R)-enantiomer of 2-amino-N-benzyl-3-methoxypropanamide, i.e. a compound of formula IIA,

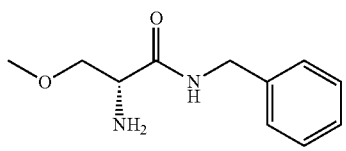

IIA forms the basis of the cation in the salt of formula I. Precipitation of the diastereomeric salt of formula I is diastereoselective, and is therefore generally not dependent on the proportions of the two enantiomers of the compound of formula II, which is usually a racemate comprising equal proportions of the (R)-enantiomer (i.e. the compound of formula IIA) and the (S)-enantiomer. In particular embodiments of the invention, the compound of formula II does not contain a significant enantiomeric excess of the (S)-enantiomer, for example the compound of formula II contains an enantiomeric excess of the (S)-enantiomer of less than 70% (such as less than 50%, 30%, 20% or 10%). In particular embodiments the compound of formula II is either a racemic mixture or contains an enantiomeric excess of the (R)-enantiomer.

In particular embodiments of the invention, the salt of formula I has (or is isolated in) a percentage diastereomeric excess of greater than 60% (such as greater than 70%, 80% or 90%). In particular embodiments the salt of formula I has (or is isolated in) a percentage diastereomeric excess of close to 100% (i.e. greater than 95%, such as greater than 96%, greater than 97%, greater than 98% or greater than 99%).

In one embodiment of the process of the invention, the process comprises the addition of a compound of formula II to a mixture of N-formyl-L-leucine and a solvent for the compound of formula II.

In a more particular embodiment of the process of the invention, the process comprises the addition of N-formyl-L-leucine to a mixture of a compound of formula II and a solvent for the compound of formula II.

Through selective isolation of the diastereomeric salt of the amine of formula IIA, the process of the invention leaves the other enantiomer (the (S)-enantiomer) of the compound of formula II in the crystallisation mixture.

Particular embodiments of the invention therefore include the step of racemising the (S)-enantiomer of the compound of formula II (i.e. converting to an equal mixture of (R)- and (S)-enantiomers). This enables isolation of further quantities of the salt of formula I.

Thus, in particular embodiments of the invention, the process of the invention is performed in the presence of a racemisation promoter (also referred to herein as "racemiser"). The racemisation of the (non-isolated) (S)-enantiomer may continue ad infinitum and hence provide (in principle) conversion of all, or substantially all, of the compound of formula II into the salt of formula I. This is depicted in the scheme below.

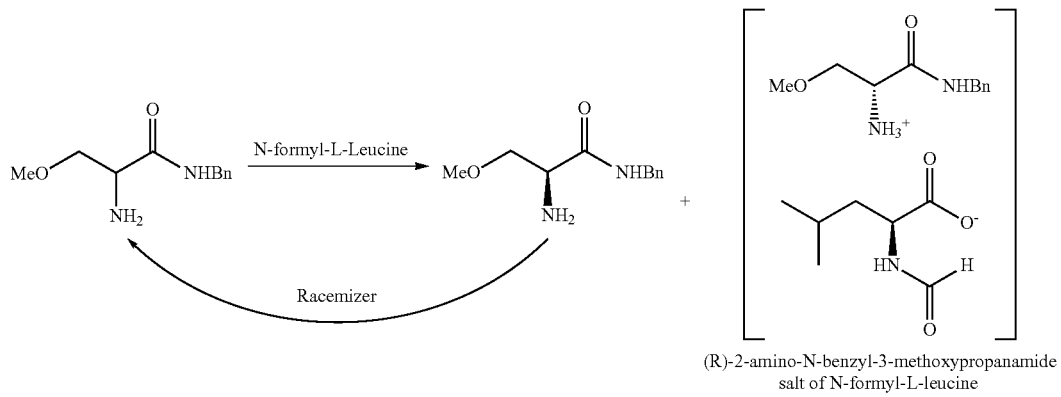

(R)-2-amino-N-benzyl-3-methoxypropanamide salt of N-formyl-L-leucine

Accordingly, in particular embodiments of the invention, the process is performed in the presence of a racemisation promoter.

The process of the invention may therefore be a dynamic resolution, which is advantageous over any known resolutions for the preparation of (R)-2-amino-N-benzyl-3-methoxypronamide (a compound of formula IIA), which may require separation (and/or isolation) of the undesired enantiomer resulting in a maximum yield of 50%. For instance, the process described in WO 2011/092559 describes a resolution (by selective precipitation) of diastereomeric salts of the two enantiomers of 2-amino-N-benzyl-3-methoxypronamide. Clearly, only a 50% yield is obtainable in this resolution step, and in fact only a 37% yield is obtained in Example 4 of WO 2011/092559. In this instance, the undesired salt of the (S)-enantiomer would have to be separated and racemised in a separate step for the further resolution to take place. Hence, in a preferred embodiment, the process of the invention is a dynamic kinetic resolution process which may take place in "one pot". By this, we mean that, in the resolution step any undesired enantiomer (of the starting material) need not be separated (and optionally recycled), but rather, in the process of the invention, the separation of the undesired enantiomer of the starting material is circumvented by its conversion to the racemate in the reaction pot (thereby allowing further selective salt formation and isolation).

The racemisation promoter may be any suitable aldehyde, ketone or metal catalyst (but preferably, it is an aldehyde). This may promote or cause the racemisation by undergoing a reversible condensation reaction, i.e. starting with a single enantiomer (or enantiomerically enriched compound) of the compound of formula II (the undesired (S)-enantiomer) and then forming a racemic mixture of the compound of formula II (or a compound of lower e.e.), such that there is more of the desired enantiomer ((R)-enantiomer) that may undergo the diastereoselective salt formation to form the single (R)-enantiomer product of formula I. The racemisation promoter (e.g. when it is a metal catalyst) may also promote or cause the racemisation by catalysing an oxidation-reduction reaction on the non-reacting amine (i.e. the (S)-enantiomer of the amine of formula II that does not precipitate during the process of the invention; e.g. involving the corresponding imine derivative). The metal catalyst system may be any suitable one that promotes the appropriate reaction (e.g. by catalyzing the oxidation-reduction) to effect the racemisation. For instance, preferably, the metal catalyst is a precious metal (e.g. palladium) on carbon.

In particular embodiments of the invention, the racemisation promoter has the formula $R^1$—CHO or $R^1$—C(O)—$R^2$;

wherein:
$R^1$ and $R^2$ independently represent
optionally substituted $C_{1-12}$ alkyl or, particularly
optionally substituted aryl or optionally substituted heteroaryl (e.g. a monocyclic aryl or monocyclic 5- or 6-membered heteroaryl group, e.g. phenyl, pyridyl and the like); the optional substituents on alkyl, aryl and heteroaryl are selected from
$T^1$ or
$C_{1-12}$ alkyl optionally substituted by one or more substituents selected from $T^2$; and
$T^1$ and $T^2$ are independently selected from
halo, —$NO_2$, —CN,
—C(O)$_2R^{x1}$,
—$OR^{x2}$, —$SR^{x3}$, —S(O)$R^{x4}$, —S(O)$_2R^{x5}$,
—N($R^{x6}$)$R^{x7}$, —N($R^{x8}$)C(O)$R^{x9}$, —N($R^{x10}$)S(O)$_2R^{x11}$,
—O—P(O)(O$R^{x12}$)(O$R^{x13}$) and
$R^{x14}$;
$R^{x1}$, $R^{x2}$, $R^{x3}$, $R^{x6}$, $R^{x7}$, $R^{x8}$, $R^{x9}$, $R^{x10}$, $R^{x12}$, and $R^{x13}$ independently represent hydrogen, $C_{1-6}$ alkyl or $C_{3-6}$ cycloalkyl, which latter two groups are optionally substituted by one or more halo atoms; and
$R^{x4}$, $R^{x5}$, $R^{x11}$ and $R^{x14}$ independently represent $C_{1-6}$ alkyl or $C_{3-6}$ cycloalkyl, which latter two groups are optionally substituted by one or more halo atoms.

Racemisation promoters that may be mentioned include:
optionally substituted salicylic aldehyde, such as unsubstituted salicylic aldehyde, dichlorosalicylic aldehyde (e.g. 3,5-dichlorosalicylic aldehyde) or 5-nitrosalicylic aldehyde;
nitro- or dinitro-benzaldehyde (e.g. 2-nitro, 4-nitro or 2,4-dinitro-benzaldehyde); and
pyridoxal-5'-phosphate (also referred to herein as "PLP").
Particular racemisation promoters that may be mentioned include those that retain or do not substantially affect the crystallisation process. These include 3,5-dichlorosalicylic aldehyde and, particularly, 5-nitrosalicylic aldehyde. Embodiments of the invention that may be mentioned therefore include those in which the racemisation promoter is dichlorosalicylic aldehyde or, particularly 5-nitrosalicylic aldehyde.

Unless otherwise specified, alkyl and alkenyl groups as defined herein may be straight-chain or, when there is a sufficient number (i.e. a minimum of three) of carbon atoms be branched-chain. Further, cycloalkyl groups as defined herein may be monocyclic or, where there is a sufficient number of carbon atoms, be bicyclic.

The term "aryl", when used herein, includes $C_{6-10}$ groups. Such groups may be monocyclic, bicyclic or tricyclic and, when polycyclic, be either wholly or partly aromatic. $C_{6-10}$ aryl groups that may be mentioned include phenyl, naphthyl, and the like. For the avoidance of doubt, the point of attachment of substituents on aryl groups may be via any carbon atom of the ring system.

The term "heteroaryl", when used herein, includes 5- to 14-membered heteroaryl groups containing one or more heteroatoms selected from oxygen, nitrogen and/or sulfur. Such heteroaryl group may comprise one, two or three rings, of which at least one is aromatic. Substituents on heteroaryl groups may, where appropriate, be located on any atom in the ring system including a heteroatom. The point of attachment of heteroaryl groups may be via any atom in the ring system including (where appropriate) a heteroatom. Examples of heteroaryl groups that may be mentioned include pyridyl, pyrrolyl, quinolinyl, furanyl, thienyl, oxadiazolyl, thiadiazolyl, thiazolyl, oxazolyl, pyrazolyl, triazolyl, tetrazolyl, isoxazolyl, isothiazolyl, imidazolyl, pyrimidinyl, indolyl, pyrazinyl, indazolyl, pyrimidinyl, quinolinyl, benzoimidazolyl and benzthiazolyl.

The term "halo", when used herein, includes fluoro, chloro, bromo and iodo.

The solvent for the compound of formula II may be an organic solvent (such as THF, aromatic hydrocarbons (e.g. toluene, xylenes, ethylbenzene, alkylbenzenes), functionalised aromatics (halobenzenes, nitrobenzenes, methoxybenzenes), 2-propanol, aliphatic hydrocarbons (e.g. methylcyclohexane or heptane(s)) or an ester (e.g. an alkenyl acetate or, particularly, an alkyl acetate such as isopropyl acetate)) or a mixture of organic solvents. In certain embodiments of the invention, the solvent for the compound of formula II is an alkyl acetate or a mixture of alkyl acetates optionally in combination with an alcohol (in particular isopropanol). For example, the solvent for the compound of formula II may be a $C_{1-12}$, $C_{1-8}$, $C_{1-6}$ alkyl acetate or, particularly, a branched $C_{3-8}$ (e.g. a branched $C_{3-4}$) alkyl acetate. In particular embodiments of the invention, the solvent for the compound of formula II is isopropyl acetate, toluene, or a mixture thereof. In another particular embodiment of the invention, the solvent for the compound of formula II is a mixture of isopropyl acetate and isopropanol. The solvent for the compound of formula II may also be a mixture of any of the above solvents, such as a mixture of aliphatic hydrocarbons, a mixture of toluene and one or more esters, or a mixture of one or more aliphatic hydrocarbons with one or more esters.

Other solvents may be present in the mixture from which the salt of formula I is isolated. However, in particular embodiments of the invention, the mixture from which the salt of formula I is isolated contains essentially no other solvents (e.g. less than 5% by weight, such as less than 4, 3, 2, 1, 0.5 or 0.1% by weight, of the mixture consists of solvents other than the solvent(s) for the compound of formula II).

The solubility of the compound of formula II in solvents such as toluene and isopropyl acetate may be improved by performing the process in the presence of a co-solvent. Co-solvents which may be used, particularly in conjunction with toluene, include DMF, DMAA (N,N-dimethylacetamide), N-methylpyrrolidone (NMP), 2-propanol or, particularly, an ether, such as THF, 2-methyl THF or methyl-tert-butyl ether (MTBE). When toluene is used as the solvent, the co-solvent to solvent ratio is typically from about 10:1 to about 1:99, preferably from about 2:1 to about 5:95.

The process of the invention may be performed at room temperature, but may be performed at elevated temperature (e.g. from ambient temperature (e.g. about 20° C.) to about 100° C. or up to about 70° C.). This will depend on the solvent system employed in the process of the invention and the boiling point thereof. In certain embodiments of the invention (e.g. when toluene and/or isopropyl acetate is employed as the solvent), the process of the invention is performed at elevated temperature (e.g. at 30° C. or above, for instance at a temperature from about 30° C. to about 100° C., particularly from about 35° C. to about 95° C.). In a particular embodiment of the invention, the process is conducted at a temperature from about 50° C. to about 80° C.

The N-formyl-L-leucine may be added in any suitable quantity, for instance from about 0.3 to 2 equivalents based on the amount of the (R)-enantiomer of the compound of formula II that is present. In certain embodiments (e.g. those in which a racemisation promoter is not used), about 1 equivalent of N-formyl-L-leucine based on the amount of the compound of formula IIA (i.e. about 0.5 equivalents of N-formyl-L-leucine based on the amount of the racemate of the compound of formula II) may be added.

In other embodiments, particularly embodiments in which a racemisation promoter is present during the salt formation, about 1 equivalent of N-formyl-L-leucine based on the amount of compound of formula II may be added.

The racemisation promoter (e.g. aldehyde as defined herein) may be added in any suitable quantity, for instance from about 0.1 to about 50 mol %, or, particularly, from about 1 to about 50 mol %, based on the quantity of the compound of formula II.

Particular embodiments of the invention that may be mentioned include those in which the racemisation promoter is used at a concentration of from about 2 to about 20 mol % (or from about 5 to about 10 mol %) relative to the compound of formula II.

The racemisation of (S)-2-amino-N-benzyl-3-methoxypropionamide to form racemic 2-amino-N-benzyl-3-methoxypropionamide can be achieved using a racemisation promoter, as indicated above, present in the amounts indicated above.

The reagents employed in the process of the invention may be introduced in any feasible, practical order.

The salt of formula I may be used to generate the amine of formula IIA. Thus, according to a third aspect of the invention, there is provided a process for preparing a compound of formula IIA, said process comprising the step of reacting a salt of formula I with a base.

The amine of formula IIA may of course be prepared from a salt of formula I that has been isolated by the process according the first aspect of the invention. In this respect, a fourth aspect of the invention provides a process for preparing a compound of formula IIA, said process comprising the steps of:
(a) isolating a salt of formula I according to the above-describe process of the first aspect of the invention; and
(b) reacting said isolated salt of formula I with a base.

In the processes of the third and fourth aspects of the invention, the base may be, for example, an inorganic base (e.g. NaOH, KOH, LiOH, Ca(OH)$_2$, Na$_2$CO$_3$, NaH, K$_2$CO$_3$, K$_3$PO$_4$, Cs$_2$CO$_3$, an alkali metal salt of an alcohol (such as t-BuONa or t-BuOK)) or an amine (such as triethylamine (TEA), pyridine, dimethylaminopyridine (DMAP), piperidine, methylpiperidine, N,N'-dimethylethylenediamine, 1,4-diazabicyclo[2.2.2]octane (DABCO) or N,N,N',N'-tetramethylethylenediamine (TMEDA)). Particular bases that may be mentioned include NaOH, KOH, LiOH and Ca(OH)$_2$.

Further, the processes of the third and fourth aspects of the invention may be conducted in the presence of a suitable solvent, such as water or, particularly, an organic solvent system. The organic solvent system may be, for example: DCM; a water immiscible alcohol (such as n-butyl alcohol, isobutyl alcohol, amyl alcohol, tert-amyl alcohol or 2-ethylhexanol); THF; acetone; ethyl ether; a mixture of methanol and ethyl ether; isopropyl acetate; toluene; methanol; methyl-tert-butyl ether; ethanol; 2-propanol; a mixture of isopropyl acetate and 2-propanol; heptane(s); or, particularly, DCM or tert-amyl alcohol.

The compound of formula IIA may be used in further reactions. For example, the primary amino moiety in that compound may be reacted with an acyl donor such as isopropenyl acetate.

Thus, according to a fifth aspect of the invention, there is provided a process for the preparation of Lacosamide (formula III):

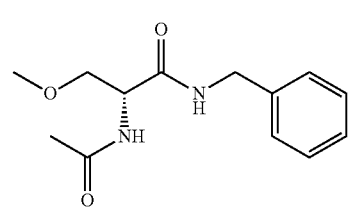

which process comprises either:
(a) a process according to the first aspect of the invention, as described above, followed by reaction of the salt of formula I with an acetyl donor optionally in the presence of a base; or
(b) a process according to the third or fourth aspects of the invention for the preparation of the compound of formula IIA, followed by reaction of that compound with an acetyl donor.

In particular embodiments of the fifth aspect of the invention, which involve the reaction of the salt of formula I with an acetyl donor, this process is performed in the presence of a base. The base may be any base as defined above in connection with the third and fourth aspects of the invention.

However, in more particular embodiments of the fifth aspect of the invention, which involve the reaction of the salt of formula I with an acetyl donor, the reaction of the salt with the acetyl donor is performed in the absence of any base.

The acetyl donor may be any compound capable of donating the acetyl ($H_3C—C(O)—$) functional group. In particular embodiments of the fifth aspect of the invention, the acetyl donor is $H_3C—C(O)$-LG, wherein LG is a suitable leaving group. Examples of LG include, for instance, —O—$R^a$ or halo (e.g. chloro), wherein $R^a$ represents, for example:

$C_{2-12}$ alkenyl, $C_{1-12}$ alkyl, $C_{3-12}$ cycloalkyl;
—C(O)—$C_{1-12}$ alkyl (e.g. —C(O)CH$_3$);
aryl; or
imidazolyl.

Particular acetyl donors that may be mentioned include compounds of formula $H_3C—C(O)—O—R^a$, wherein $R^a$ represents, for example, —C(O)CH$_3$, branched or linear $C_{1-8}$ (e.g. $C_1$, $C_2$, $C_3$ or $C_4$) alkyl or, particularly, branched or linear $C_{2-8}$ (e.g. $C_2$, $C_3$ or $C_4$) 1-alkenyl. Thus, particular embodiments of the fifth aspect of the invention that may be mentioned include those in which the acetyl donor is acetic anhydride, isopropenyl acetate or vinyl acetate.

The acetylation reaction may be performed in the presence of a suitable solvent, for example an organic solvent (such as DCM; a water immiscible alcohol (such as n-butyl alcohol, isobutyl alcohol, amyl alcohol, tert-amyl alcohol or 2-ethylhexanol); THF, toluene, 2-propanol or an ester (e.g. an alkyl or alkenyl acetate such as isopropyl acetate)) or a mixture of organic solvents. Alternatively, the suitable solvent may be a mixture of water and one or more such organic solvents. In certain embodiments (e.g. when the acetyl donor is a $C_{2-12}$ 1-alkenyl acetate, such as isopropenyl acetate or vinyl acetate), the acetyl donor itself may act as a solvent or co-solvent for the acetylation reaction. In particular embodiments of the fifth aspect of the invention, the acetyl donor is isopropenyl acetate and the solvent for the acetylation is either isopropenyl acetate or, particularly, a mixture of isopropyl acetate and isopropenyl acetate.

Acetylation using a $C_{2-12}$ 1-alkenyl acetate (e.g. a $C_2$ or, particularly, $C_3$ 1-alkenyl acetate, such as isopropenyl acetate) as both acetyl donor and (co-)solvent may have the advantage that the compound of formula III can be isolated from the reaction mixture by simple techniques, such as filtration. This can therefore increase the overall yield of the compound of formula III by eliminating the need for more involved work-up procedures (e.g. as those involving washing out side-products with water or an aqueous solution, such as brine).

In a further particular embodiment, the acetyl donor may be acetic anhydride, and the solvent for the acetylation reaction may be water optionally in the presence of one or more organic solvents (such as dichloromethane and/or a water immiscible alcohol). When acetic anhydride is used as an acetyl donor, a particular solvent mixture that may be mentioned is a mixture of water with either dichloromethane or tert-amyl alcohol.

The N-formyl-L-leucine present in the salt of formula I may optionally be recovered from the reactions involving the formation of the compounds of formulae IIA or III therefrom. The N-formyl-L-leucine may be so recovered by, for example, combining the resulting media from those reactions (typically aqueous media) containing N-formyl-L-leucine, acidifying that media (e.g. by addition of an inorganic acid, such as HCl) in order to obtain a suitable pH of the solution and allow the precipitation of the N-formyl-L-leucine as a salt, and isolating the solid N-formyl-L-leucine that is so obtained (e.g. by filtration).

Thus in an embodiment of the third and fourth aspects of the invention there is provided a process for the preparation of a compound of formula IIA, which process further comprises the step of recovering the N-formyl-L-leucine from the reaction media.

Similarly, in an embodiment of the fifth aspect of the invention there is provided a process for the preparation of Lacosamide (formula III), which process further comprises the step of recovering the N-formyl-L-leucine from the reaction media.

Lacosamide prepared according to the present invention may be formulated for delivery to a patient by admixing with one or more pharmaceutically acceptable adjuvants, diluents and/or carriers. Thus, according to a sixth aspect of the invention, there is provided a process for preparing a pharmaceutical formulation comprising Lacosamide, said process comprising a process according to the fifth aspect of the invention, as described above, followed by admixing the Lacosamide with one or more pharmaceutically acceptable adjuvants, diluents and/or carriers and, optionally, one or more other pharmacologically active agents.

Additionally, the Lacosamide prepared according to the present invention may be obtained in a particular polymorphic form, for example a form useful in formulating Lacosamide for delivery to a patient according to the sixth aspect of the invention.

Polymorphic forms of Lacosamide can be distinguished by reference to their onset of melting, powder X-ray diffraction patterns, and/or single crystal X-ray data. One particular polymorph of Lacosamide of interest has an onset of melting which is in the range of 143 to 148° C., for example about 146° C. when it is substantially pure. This polymorph, when it is substantially pure, also has an X-ray powder diffraction pattern containing specific peaks of high intensity at 8.4° (±0.1°), 13.1° (±0.1°), 20.9° (±0.1°), 21.5° (±0.1°), 25.0° (±0.1°) and 25.4° (±0.1°) 2θ (2-theta).

The formation of a polymorph of Lacosamide having the above characteristic X-ray powder diffraction pattern and/or onset of melting may be achieved through crystallisation from a solution of Lacosamide in isopropyl acetate. This polymorph of Lacosamide may also be advantageously obtained by crystallisation from the reaction mixture that is itself obtained during the formation of Lacosamide (e.g. the mixture that is obtained during the formation of Lacosamide according to the fifth aspect of the invention).

Therefore, according to a seventh aspect of the invention, there is provided a process for the preparation of a polymorph of Lacosamide having the characteristic powder X-ray diffraction pattern peaks and/or temperature of onset of melting as specified above, which process comprises the crystallisation of Lacosamide in a suitable solvent, such as an ester (for example, a $C_{1-6}$ alkyl ester (e.g. ethyl acetate or, particularly, isopropyl acetate)). In one embodiment of this aspect of the invention, the Lacosamide is first obtained from the salt of formula I (e.g. by a process as defined according to the fifth aspect of the invention), optionally wherein the salt of formula I is itself obtained from a compound of formula II by a process as defined according to the first aspect of the invention.

Compounds of formula II may be prepared by reduction of a compound of formula IV,

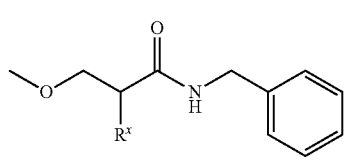

IV wherein R^x represents —N_3, or another appropriate group that may undergo reduction to form a —NH_2 moiety (e.g. —N(H)—C(H)(R^{20})R^{21}; in which one of R^{20} and R^{21} represents optionally substituted aryl or optionally substituted heteroaryl (e.g. optionally substituted aryl/heteroaryl) and the other represents hydrogen, optionally substituted $C_{1-12}$ alkyl or optionally substituted aryl or optionally substituted heteroaryl (e.g. optionally substituted aryl/heteroaryl); e.g. R^x may represent —N(H)—CH_2-aryl or —N(H)—C(H)-(aryl)_2, such as —N(H)—CH_2-phenyl) for instance, under appropriate conditions, e.g. reduction by hydrogenation (or hydrogenolysis), in the presence of hydrogen gas (or a source of hydrogen), in the presence of an appropriate catalyst system (e.g. a precious metal catalyst, such as Pd/C).

In particular embodiments, compounds of formula II may be prepared by reduction of a compound of formula IV, in which R^x represents —N_3, or another appropriate group that may undergo reduction to form a —NH_2 moiety (e.g. —N(H)—C(H)(R^{20})R^{21}; in which one of R^{20} and R^{21} represents optionally substituted aryl/heteroaryl) and the other represents hydrogen, optionally substituted $C_{1-12}$ alkyl or optionally substituted aryl/heteroaryl, under appropriate reducing conditions, as described above.

In particular embodiments of the above processes, the optional substituents are selected from: T^3 or $C_{1-12}$ alkyl optionally substituted by one or more substituents selected from T^4; in which:

T^3 and T^4 are independently selected from halo, —NO_2, —CN, —C(O)_2R^{y1}, —OR^{y2}, —SR^{y3}, —S(O)R^{y4}, —S(O)_2R^{y5}, —N(R^{y6})R^{y7}, —N(R^{y8})C(O)R^{y9}, —N(R^{y10})S(O)_2R^{y11}, —O—P(O)(OR^{y12})(OR^{y13}) or R^{y14};

R^{y1}, R^{y2}, R^{y3}, R^{y6}, R^{y7}, R^{y8}, R^{y9}, R^{y10}, R^{y12} and R^{y13} independently represent hydrogen or $C_{1-6}$ alkyl optionally substituted by one or more halo atoms;

R^{y4}, R^{y5}, R^{y11} and R^{y14} independently represent $C_{1-6}$ alkyl optionally substituted by one or more halo atoms.

Thus according to an eighth aspect of the invention, there is provided a process for preparing a compound of formula II, as defined above, said process comprising the reduction of a compound of formula IV, as defined above. Such methods, particularly those involving the formation of a compound of formula IV in which R^x represents —NH-benzyl, can be advantageous in that they do not require cumbersome separation techniques (including distillation) in order to separate the product from any unwanted by-products or unreacted starting materials prior to any subsequent reactions.

In further embodiments of this aspect of the invention, compounds of formula II, which are prepared by the reduction of a compound of formula IV according to a process as defined above, may be used in the preparation of Lacosamide. The preparation of Lacosamide from the compound of formula II may optionally also involve an intermediate step of isolating a salt of formula I as defined in the first aspect of the invention.

Thus there is provided a process for the preparation of Lacosamide, which process comprises the reduction of a compound of formula IV to produce a compound of formula II, according to a process as defined above, followed by the preparation of Lacosamide from the compound of formula II, optionally wherein the preparation of Lacosamide also involves:

(a) the isolation of a salt of formula I according to the first aspect of the invention, as described above, and/or (b) the formation of Lacosamide from a salt of formula I according to the fifth aspect of the invention, as described above.

Compounds of formula II may also be prepared by reaction of a compound of formula V,

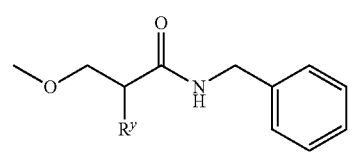

V wherein R^y represents a suitable leaving group, such as halo (in particular, chloro), with ammonia, under appropriate conditions, for example as described in WO 2010/052011.

Compounds of formula IV may be prepared by reaction of a compound of formula VI,

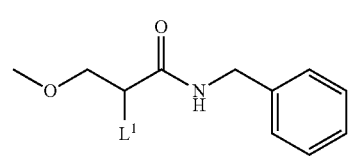

VI wherein L^1 represents a suitable leaving group, e.g. a sulfonate group or preferably a halo group (e.g. bromo or, particularly, chloro), in the presence of an appropriate amine donor (or group that allows the introduction of the R^x moiety), e.g. an azide (e.g. an inorganic metal azide, e.g. sodium azide) or the appropriate amine (e.g. H_2N—C(H)(R^{20})R^{21}, such as benzylamine), under appropriate conditions, for example in the presence of a suitable solvent system (e.g. water or an organic solvent (such as 2-propanol), or mixtures thereof).

Compounds of formula IV in which R^x represents NH-benzyl may also be prepared by reaction of a compound of formula VII,

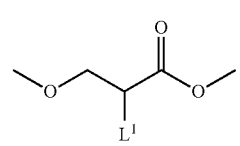

VII wherein L^1 represents a suitable leaving group, e.g. a sulfonate group or preferably a halo group (e.g. bromo or, particularly, chloro), in the presence of benzylamine, under appropriate conditions, for example in the presence of a suitable solvent system (e.g. water or an organic solvent (such as 2-propanol), or mixtures thereof).

Thus according to a ninth aspect of the invention, there is provided a process for preparing a compound of formula IV, as defined above, said process comprising the reaction of a compound of formula VII, as defined above, in the presence of benzylamine.

In further embodiments of this aspect of the invention, compounds of formula IV, which are prepared by the reaction of compounds of formula VII according to a process as defined above, may be used in the preparation of Lacosamide. The preparation of Lacosamide starting from the compound of formula IV may optionally also involve the intermediate step of isolating a salt of formula I as defined in the first aspect of the invention.

Thus there is provided a process for the preparation of Lacosamide, which process comprises the reaction of a compound of formula VII to produce a compound of formula IV according to a process as defined above, followed by preparation of Lacosamide from the compound of formula IV. In an embodiment of this process for the preparation of Lacosamide, the process further involves:
  (a) the reduction of the compound of formula IV to produce a compound of formula II according to the eighth aspect of the invention, as described above;
  (b) the isolation of a salt of formula I according to the first aspect of the invention, as described above; and/or
  (c) the formation of Lacosamide from a salt of formula I according to the fifth aspect of the invention, as described above.

In a particular embodiment of this process, the process for the preparation of Lacosamide comprises:
  (a) the reaction of a compound of formula VII to produce a compound of formula IV according to a process described above;
  (b) the reduction of the compound of formula IV so formed to produce a compound of formula II according to the eighth aspect of the invention, as described above;
  (c) the isolation of a salt of formula I according to the first aspect of the invention, as described above; and
  (d) the formation of Lacosamide from a salt of formula I according to the fifth aspect of the invention, as described above.

Compounds of formula VI in which $L^1$ represents halo group (e.g. bromo or, particularly, chloro) may be prepared in accordance with the procedures described in international patent application WO 2010/052011. Alternatively and advantageously, such compounds may be prepared by reaction of a compound of formula VIII,

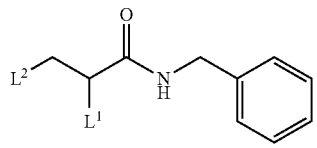

VIII wherein $L^2$ represents a suitable leaving group such as one hereinbefore defined by $L^1$ (e.g. both $L^1$ and $L^2$ may represent bromo), in the presence of a suitable reagent/conditions that promotes the nucleophilic substitution of the $L^2$ group with a methoxy group (e.g. regioselectively). For instance, the reaction may be performed in the presence of methanol in an appropriate base (e.g. an alkali metal hydroxide, e.g. sodium hydroxide).

Compounds of formula VII in which $L^1$ represents halo group (e.g. bromo or, particularly, chloro) may be prepared by reaction of a compound of formula IX,

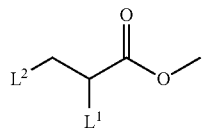

IX wherein $L^2$ represents a suitable leaving group such as one hereinbefore defined by $L^1$ (e.g. both $L^1$ and $L^2$ may represent chloro or bromo), in the presence of a suitable reagent/conditions that promotes the nucleophilic substitution of the $L^2$ group with a methoxy group (e.g. regioselectively), for example in accordance with the procedures described in DE 1028557. For instance, the reaction may be performed in the presence of methanol in an appropriate base (e.g. an alkali metal methoxide, e.g. sodium methoxide).

Thus according to a tenth aspect of the invention, there is provided a process for preparing a compound of formula VII, as defined above, said process comprising the reaction of a compound of formula IX, as defined above, in the presence of a suitable reagent/conditions that promotes the nucleophilic substitution of the $L^2$ group with a methoxy group.

In further embodiments of this aspect of the invention, compounds of formula VII, which are prepared by the reaction of compounds of formula IX according to a process as defined above, may be used in the preparation of Lacosamide. The preparation of Lacosamide from the compound of formula VII may optionally also involve an intermediate step of isolating a salt of formula I as defined in the first aspect of the invention.

Thus there is provided a process for the preparation of Lacosamide, which process comprises the reaction of a compound of formula IX to produce a compound of formula VII according to a process as defined above, followed by preparation of Lacosamide from the compound of formula VII. In an embodiment of this process for the preparation of Lacosamide, the process further involves:
  (a) the reaction of the compound of formula VII to produce a compound of formula IV according to the ninth aspect of the invention, as described above;
  (b) the reduction of a compound of formula IV to produce a compound of formula II according to the eighth aspect of the invention, as described above;
  (c) the isolation of a salt of formula I according to the first aspect of the invention, as described above; and/or
  (d) the formation of Lacosamide from a salt of formula I according to the fifth aspect of the invention, as described above.

In a particular embodiment of this process, the process for the preparation of Lacosamide comprises:
  (a) the reaction of a compound of formula IX to produce a compound of formula VII according to the process described above;
  (b) the reaction of the compound of formula VII so formed to produce a compound of formula IV according to the ninth aspect of the invention, as described above;
  (c) the reduction of the compound of formula IV so formed to produce a compound of formula II according to the eighth aspect of the invention, as described above;
  (d) the isolation of a salt of formula I according to the first aspect of the invention, as described above; and
  (e) the formation of Lacosamide from a salt of formula I according to the fifth aspect of the invention, as described above.

In a further particular embodiment of the invention, there is provided a process for preparing a polymorph of Lacosamide having an X-ray powder diffraction pattern containing specific peaks of high intensity at 8.4° (±0.1°), 13.1° (±0.1°), 20.9° (±0.1°), 21.5° (±0.1°), 25.0° (±0.1°) and 25.4° (±0.1°) 2θ, which process comprises the following steps:

(a) reacting a compound of formula IX, as defined above, wherein $L^1$ and $L^2$ independently represent a halogen atom, according to any of the processes defined above to produce a compound of formula IV, as defined above, wherein $R^x$ represents a NH-benzyl group;

(b) reducing the compound of formula IV obtained in step (a) to produce a compound of formula II according to the eighth aspect of the invention, as described above;

(c) isolating a salt of formula I according to the first aspect of the invention, as described above, using the compound of formula II as formed in step (b);

(d) reacting the product obtained in step (c) with an acetyl donor, optionally in the presence of a base, to form Lacosamide according to the fifth aspect of the invention, as described above; and (e) crystallising the product obtained in step (d) in a suitable solvent, according to the seventh aspect of the invention, as described above.

Compounds of formula IX in which $L^1$ and $L^2$ represent the same halo group (e.g. both $L^1$ and $L^2$ represent bromo) may be prepared by reaction of methyl acrylate with a source of halogen (e.g. $Br_2$ or N-bromosuccinimide) in the presence of a suitable reagent that promotes the halogenation of the alkene portion of the acrylate group.

Compounds employed in or produced by the processes described herein (i.e. those involving the process of the invention) may exhibit tautomerism. The process of the invention therefore encompasses the use or production of such compounds in any of their tautomeric forms, or in mixtures of any such forms.

Further, the compounds employed in or produced by the processes described herein may contain double bonds and may thus exist as E (entgegen) and Z (zusammen) geometric isomers about each individual double bond. All such isomers and mixtures thereof are included within the scope of the invention.

Some intermediate compounds disclosed herein may be novel (and useful in the processes described herein). Other intermediate compounds, and derivatives thereof (e.g. protected derivatives), may be commercially available, are known in the literature or may be obtained by conventional synthetic procedures, in accordance with known techniques, from readily available starting materials using appropriate reagents and reaction conditions.

It will also be appreciated by those skilled in the art that, in the processes described above, functional groups of intermediate compounds may be, or may need to be, protected by protecting groups.

The protection and deprotection of functional groups may take place before or after any of the reaction steps described hereinbefore.

Protecting groups may be removed in accordance with techniques which are well known to those skilled in the art and as described hereinafter.

The use of protecting groups is described in "Protective Groups in Organic Chemistry", edited by J. W. F. McOmie, Plenum Press (1973), and "Protective Groups in Organic Synthesis", 3rd edition, T. W. Greene & P. G. M. Wutz, Wiley-Interscience (1999).

In certain embodiments of the invention, the process of the invention may be advantageously performed without separation (e.g. isolation) of any side-products or undesired products.

The processes described herein may be operated as a batch process or operated as a continuous process and may be conducted on any scale.

Embodiments

Embodiments of the invention that may be mentioned include those described above, in the examples below, and in the attached claims. For the avoidance of doubt, such embodiments include the following.

(1) A salt of formula I,

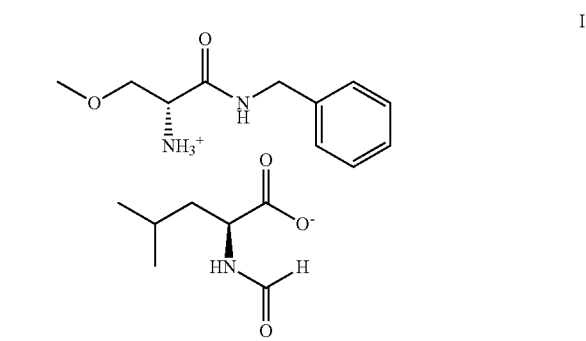

or a solvate thereof.

(2) A process for the isolation of salt of formula I, as defined in Embodiment 1, which process comprises precipitation of the salt of formula I from a mixture of N-formyl-L-leucine, a compound of formula II,

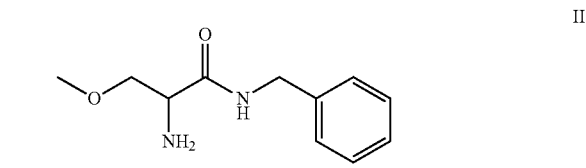

and a solvent for the compound of formula II.

(3) The salt of formula I according to Embodiment 1, or the process according to Embodiment 2, wherein the salt of formula I has (or is isolated in) a percentage diastereomeric excess of greater than 60% (such as greater than 70%, 80% or 90%).

(4) The salt or process according to Embodiment 3, wherein the salt of formula I has (or is isolated in) a percentage diastereomeric excess of greater than 95% (e.g. greater than 96%, greater than 97%, greater than 98% or, particularly, greater than 99%).

(5) The process according to any of Embodiments 2 to 4, wherein the compound of formula II is racemic.

(6) The process according to any of Embodiments 2 to 5, wherein the N-formyl-L-leucine has a percentage enantiomeric excess of the L-enantiomer of greater than 60% (e.g. greater than 70%, 80%, 90%, 95% or 99%).

(7) The process according to any of Embodiments 2 to 5, wherein the process comprises the addition of a compound of formula II to a mixture of N-formyl-L-leucine and a solvent for the compound of formula II.

(8) The process according to any of Embodiments 2 to 5, wherein the process comprises the addition of N-formyl-L-leucine to a mixture of a compound of formula II and a solvent for the compound of formula II.

(9) The process according to any of Embodiments 2 to 8, wherein the process is performed in the presence of a racemisation promoter.

(10) The process according to Embodiment 9, wherein the racemisation promoter is an aldehyde, ketone or metal catalyst.

(11) The process according to Embodiment 9, wherein the racemisation promoter has the formula

or

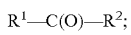

wherein:
$R^1$ and $R^2$ independently represent
optionally substituted $C_{1-12}$ alkyl or, particularly
optionally substituted aryl or optionally substituted heteroaryl (e.g. a monocyclic aryl or monocyclic 5- or 6-membered heteroaryl group, e.g. phenyl, pyridyl and the like);
the optional substituents on alkyl, aryl and heteroaryl are selected from
$T^1$ or
$C_{1-12}$ alkyl optionally substituted by one or more substituents selected from $T^2$; and
$T^1$ and $T^2$ are independently selected from
halo, $-NO_2$, $-CN$,
$-C(O)_2R^{x1}$,
$-OR^{x2}$, $-SR^{x3}$, $-S(O)R^{x4}$, $-S(O)_2R^{x5}$,
$-N(R^{x6})R^{x7}$, $-N(R^{x8})C(O)R^{x9}$, $-N(R^{x10})S(O)_2R^{x11}$,
$-O-P(O)(OR^{x12})(OR^{x13})$ and
$R^{x14}$;
$R^{x1}$, $R^{x2}$, $R^{x3}$, $R^{x6}$, $R^{x7}$, $R^{x8}$, $R^{x9}$, $R^{x10}$, $R^{x12}$, and $R^{x13}$ independently represent hydrogen, $C_{1-6}$ alkyl or $C_{3-6}$ cycloalkyl, which latter two groups are optionally substituted by one or more halo atoms; and
$R^{x4}$, $R^{x5}$, $R^{x11}$ and $R^{x14}$ independently represent $C_{1-6}$ alkyl or $C_{3-6}$ cycloalkyl, which latter two groups are optionally substituted by one or more halo atoms.

(12) The process according to Embodiment 9, wherein the racemisation promoter is selected from salicylic aldehyde, dichlorosalicylic aldehyde (e.g. 3,5-dichlorosalicylic aldehyde), 5-nitrosalicylic aldehyde, nitro- or dinitrobenzaldehyde (e.g. 2-nitro, 4-nitro or 2,4-dinitro-benzaldehyde) and pyridoxal-5'-phosphate.

(13) The process according to Embodiment 9, wherein the racemisation promoter is 3,5-dichlorosalicylic aldehyde or 5-nitrosalicylic aldehyde.

(14) The process according to Embodiment 9, wherein the racemisation promoter is 5-nitrosalicylic aldehyde.

(15) The process according to any one of Embodiments 9 to 14, wherein the racemisation promoter is present at about 0.1 to about 50 mol % (e.g. from about 1 to about 50 mol %) relative to the compound of formula II.

(16) The process according to any one of Embodiments 9 to 15, wherein the racemisation promoter is present at about 2 to about 20 mol % (e.g. from about 5 to about 10 mol %) relative to the compound of formula II.

(17) The process according to any one of Embodiments 2 to 16, wherein the solvent for the compound of formula II is one or more organic solvents selected from THF, aromatic hydrocarbons (e.g. toluene, xylenes, ethylbenzene, alkylbenzenes), functionalised aromatics (halobenzenes, nitrobenzenes, methoxybenzenes), 2-propanol, aliphatic hydrocarbons (e.g. methylcyclohexane or heptane(s)) or an ester (e.g. an alkenyl acetate or, particularly, an alkyl acetate such as isopropyl acetate)).

(18) The process according to any one of Embodiments 2 to 17, wherein the solvent for the compound of formula II is an alkyl acetate (e.g. a $C_{1-12}$, $C_{1-8}$, $C_{1-6}$ alkyl acetate or, particularly, a branched $C_{3-8}$ (e.g. a branched $C_{3-4}$) alkyl acetate) or a mixture of alkyl acetates; or wherein the solvent for the compound of formula II is a mixture of one of said alkyl acetates (preferably isopropyl acetate) and isopropanol.

(19) The process according to any one of Embodiments 2 to 18, wherein the solvent for the compound of formula II is toluene.

(20) The process according to any one of Embodiments 2 to 19, wherein the process is conducted at a temperature from ambient temperature (e.g. about 20° C.) to about 100° C. (e.g. from about 20° C. to about 70° C.).

(21) The process according to any one of Embodiments 2 to 20, wherein the process is conducted at a temperature from about 30° C. to about 100° C. (e.g. from about 35° C. to about 95° C., from about 30° C. to about 80° C., or from about 50° C. to about 80° C).

(22) The process according to any one of Embodiments 2 to 21, wherein N-formyl-L-leucine is present at about 0.3 to 2 equivalents (e.g. about 0.5 equivalents or 1 equivalent) relative to the amount of the (R)-enantiomer of the compound of formula II that is present.

(23) A process for preparing a compound of formula IIA,

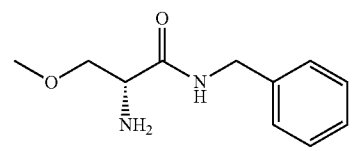

said process comprising the step of reacting a salt of formula I, as defined in any one of Embodiments 1, 3 and 4, with a base.

(24) A process for preparing a compound of formula IIA, as defined in Embodiment 23, said process comprising the steps of:
(a) isolating a salt of formula I according to a process as defined in any one of Embodiments 2 to 22; and
(b) reacting said isolated salt of formula I with a base.

(25) A process according to Embodiment 23 or Embodiment 24, wherein the process is conducted in the presence of a solvent, such as water or, particularly, an organic solvent system.

(26) A process according to Embodiment 25, wherein the organic solvent system is: DCM; a water immiscible alcohol (such as n-butyl alcohol, isobutyl alcohol, amyl alcohol, tert-amyl alcohol or 2-ethylhexanol); THF; acetone; ethyl ether; a mixture of methanol and ethyl ether; isopropyl acetate; toluene; methanol; 2-propanol; methyl-tert-butyl ether; ethanol; a mixture of isopropyl acetate and 2-propanol; heptane(s); or, particularly, DCM or tert-amyl alcohol.

(27) A process for the preparation of Lacosamide (formula III):

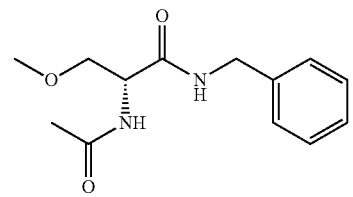

which process comprises either:
   (a) a process as defined in any one of Embodiments 2 to 22, followed by reaction of the salt of formula I with an acetyl donor optionally in the presence of a base; or
   (b) a process as defined in any one of Embodiments 23 to 26, followed by reaction of the compound of formula IIA with an acetyl donor.
(28) A process according to any one of Embodiments 23 to 27, wherein the base is an inorganic base (e.g. NaOH, KOH, LiOH, Ca(OH)$_2$, Na$_2$CO$_3$, NaH, K$_2$CO$_3$, K$_3$PO$_4$, Cs$_2$CO$_3$, an alkali metal salt of an alcohol (such as t-BuONa or t-BuOK)) or an amine (such as triethylamine (TEA), pyridine, dimethylaminopyridine (DMAP), piperidine, methylpiperidine, N,N'-dimethylethylenediamine, 1,4-diazabicyclo[2.2.2]octane (DABCO) or N,N,N',N'-tetramethylethylenediamine (TMEDA)).
(29) A process according to Embodiment 27 wherein the base is selected from the group consisting of NaOH, KOH, LiOH and Ca(OH)$_2$.
(30) A process according to any one of Embodiments 27 to 29, wherein the acetyl donor has the formula H$_3$C—C(O)-LG, wherein LG is a leaving group.
(31) A process according to Embodiment 30, wherein LG is —O—R$^a$ or halo (e.g. chloro), wherein R$^a$ represents:
   C$_{2-12}$ alkenyl, C$_{1-12}$ alkyl, C$_{3-12}$ cycloalkyl;
   —C(O)—C$_{1-12}$ alkyl (e.g. —C(O)CH$_3$);
   aryl; or
   imidazolyl.
(32) A process according to any one of Embodiments 27 to 31, wherein the acetyl donor has the formula H$_3$C—C(O)—O—R$^a$, wherein R$^a$ represents —C(O)CH$_3$, branched or linear C$_{1-8}$ (e.g. C$_1$, C$_2$, C$_3$ or C$_4$) alkyl or, particularly, branched or linear C$_{2-8}$ (e.g. C$_2$, C$_3$ or C$_4$) 1-alkenyl.
(33) A process according to any one of Embodiments 27 to 32, wherein the acetyl donor is acetic anhydride, isopropenyl acetate or vinyl acetate.
(34) A process according to any one of Embodiments 27 to 33, wherein the acetyl donor is acetic anhydride.
(35) A process according to any one of Embodiments 27 to 34, wherein the acetylation reaction is performed in the presence of a solvent that is a C$_{1-12}$ alkyl acetate, a C$_{2-12}$ 1-alkenyl acetate, or a mixture thereof (e.g. isopropenyl acetate or, particularly, a mixture of isopropyl acetate and isopropenyl acetate).
(36) A process according to Embodiment 35, wherein the solvent for the reaction is water optionally in the presence of one or more organic solvents (such as dichloromethane and/or a water immiscible alcohol).
(37) A process according to Embodiment 36, wherein the solvent for the reaction is a mixture of water with either dichloromethane or tert-amyl alcohol.
(38) A process for preparing a pharmaceutical formulation comprising Lacosamide, said process comprising a process according to any one of Embodiments 27 to 37, followed by admixing the Lacosamide with one or more pharmaceutically acceptable adjuvants, diluents and/or carriers and, optionally, one or more other pharmacologically active agents.
(39) The process according to Embodiment 38, wherein the Lacosamide is admixed with one or more pharmaceutically acceptable adjuvants, diluents and/or carriers.

(40) A process for preparing a compound of formula II,

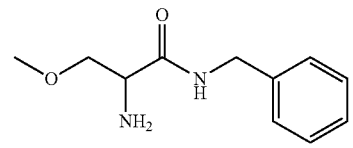

II said process comprising the reduction of a compound of formula IV,

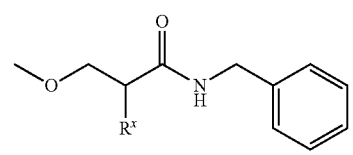

IV wherein R$^x$ represents —N$_3$, or another appropriate group that may undergo reduction to form a —NH$_2$ moiety.

(41) A process for preparing a compound of formula IV,

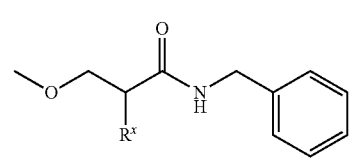

IV wherein R$^x$ represents —N$_3$, or another appropriate group that may undergo reduction to form a —NH$_2$ moiety, said process comprising the reaction of a compound of formula VII,

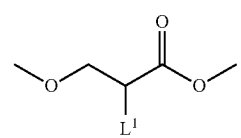

VII wherein L$^1$ represents a suitable leaving group, with benzylamine.

(42) A process for preparing a compound of formula VII,

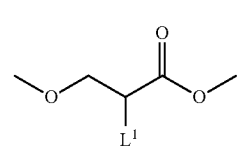

VII wherein L$^1$ represents a suitable leaving group, said process comprising the reaction of a compound of formula IX,

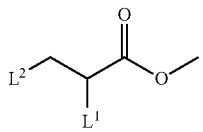

IX wherein $L^1$ and $L^2$ independently represent a suitable leaving group, in the presence of a suitable reagent and/or conditions that promotes the nucleophilic substitution of the $L^2$ group with a methoxy group.

(43) A process for preparation of Lacosamide, which process comprises the reduction of a compound of formula IV to produce a compound of formula II, according to a process as defined in Embodiment 40, followed by preparation of Lacosamide from the compound of formula II, optionally wherein the preparation of Lacosamide also involves:
  (a) the isolation of a salt of formula I, as described in Embodiment 2, and/or
  (b) the formation of Lacosamide from a salt of formula I, as described in Embodiment 27.

(44) A process for the preparation of Lacosamide, which process comprises the reaction of a compound of formula VII to produce a compound of formula IV according to a process as defined in Embodiment 41, followed by preparation of Lacosamide from the compound of formula IV, optionally wherein the process further involves:
  (a) the reduction of the compound of formula IV to produce a compound of formula II, as described in Embodiment 40;
  (b) the isolation of a salt of formula I, as described in Embodiment 2; and/or
  (c) the formation of Lacosamide from a salt of formula I, as described in Embodiment 27.

(45) A process for the preparation of Lacosamide, which process comprises the reaction of a compound of formula IX to produce a compound of formula VII according to a process as defined in Embodiment 42, followed by preparation of Lacosamide from the compound of formula VII, optionally wherein the process further involves:
  (a) the reaction of the compound of formula VII to produce a compound of formula IV as described in Embodiment 41;
  (b) the reduction of a compound of formula IV to produce a compound of formula II, as described in Embodiment 40;
  (c) the isolation of a salt of formula I, as described in Embodiment 2; and/or
  (d) the formation of Lacosamide from a salt of formula I, as described in Embodiment 27.

(46) A process as described in any one of Embodiments 27 to 37 and 43 to 45 wherein the Lacosamide so produced is subsequently crystallised from a suitable solvent.

(47) A process according to Embodiment 46, wherein the solvent is a $C_{1-6}$ alkyl ester.

(48) A process according to Embodiment 47, wherein the solvent is isopropyl acetate.

(49) A process for preparing a pharmaceutical formulation comprising Lacosamide, said process comprising a process according to any one of Embodiments 46 to 48, followed by admixing the crystallised Lacosamide with one or more pharmaceutically acceptable adjuvants, diluents and/or carriers and, optionally, one or more other pharmacologically active agents.

In general, the processes described herein, may have the advantage that the compounds of formula I may be produced in a manner that utilises fewer reagents and/or solvents, and/or requires fewer reaction steps (e.g. distinct/separate reaction steps) compared to processes disclosed in the prior art. Processes described herein may also have the advantage that fewer undesired by-products (resultant of undesired side reactions) may be produced, for example, by-products that may be toxic or otherwise dangerous to work with, e.g. explosive.

In addition, the processes described herein may be capable of being carried out in the same solvent system. This is advantageous as it limits the need for expensive, time consuming and wasteful workup procedures to recover the intermediate products from the reaction media. For example, a number of processes described herein may be carried out in a solvent system that is predominantly comprised of isopropyl acetate (or predominantly comprised of a mixture of isopropyl acetate and isopropanol), as can be seen in certain Examples below.

The processes of the invention may also have the advantage that the compound of formula I is produced in higher yield, in higher purity, in higher selectivity (e.g. higher regioselectivity), in less time, in a more convenient (i.e. easy to handle) form, from more convenient (i.e. easy to handle) precursors, at a lower cost and/or with less usage and/or wastage of materials (including reagents and solvents) compared to the procedures disclosed in the prior art. Furthermore, there may be several environmental benefits of the process of the invention.

A particular benefit of using N-formyl-L-leucine is that the amino acid derivative is derived from the natural form of leucine (L-leucine) and thus is more cheaply and more readily available compared to D-leucine and its derivatives.

A particular benefit of preparing the salt of formula I starting from the compound of formulae IX, VII or IV is that it is not necessary to isolate the intermediate compounds that are obtained during this multi-step process. Indeed, many of these reactions may be performed sequentially using essentially the same solvent system (particularly a solvent system that is predominantly comprised of isopropyl acetate or, for the step of forming the salt of formula I, a mixture of isopropyl acetate with isopropanol).

Similarly, the two-step process of preparing crystallised Lacosamide from the salt of formula I can involve the same solvent system in both steps (particularly a solvent system that is predominantly comprised of isopropyl acetate).

Thus, processes such as these (i.e. so-called "telescoped" processes) can allow the use of manufacturing practices that are substantially more efficient, result in high yields, and/or give products having high enantiomeric purities (where relevant), compared to the processes of the prior art.

EXAMPLES

The following examples are merely illustrative examples of the processes of the invention described herein.

All equipment, reagents and solvents used were standard laboratory equipment, e.g. glassware, heating apparatus and HPLC apparatus.

Example 1

Isolation of
(R)-2-amino-N-benzyl-3-methoxypropanamide
without the use of a racemiser Crude racemic 2-amino-N-benzyl-3-methoxypropanamide (assay 82.5%; 5.9 g) was dissolved in isopropyl acetate (150 mL). (S)-2-Formamido-4-methylpentanoic acid (1.90 g; 0.5 eq.) was added. The suspension was heated at stirring to 82° C. A thick white slurry was formed. More isopropyl acetate (50 mL) was added. The suspension was heated to reflux in 10 minutes and then allowed to cool to 27° C. and filtered. The filter cake was washed with isopropyl acetate (10 mL). A fine white solid was obtained; dry weight 4.0 g; chiral HPLC: 93% of (R)-enantiomer, 7% of (S)-enantiomer; calculated yield of (R)-enantiomer 86%. The crude product was re-crystallized from isopropyl acetate (50 mL) n-butanol (50 mL) to obtain 3.0 g of solid (99.8% of (R)-enantiomer, 0.2% of (S)-enantiomer). Free base (R)-2-amino-N-benzyl-3-methoxypropanamide was obtained by extraction of the alkaline salt solution in water with methylene chloride and evaporation of the solvent. An almost colourless liquid, 1.59 g was obtained with 99.3% purity by HPLC area %. Chiral purity: 98.7% of (R)-enantiomer, 1.3% of (S)-enantiomer.

Example 2

Isolation of (R)-2-amino-N-benzyl-3-methoxypropanamide using a racemiser

Racemic 2-amino-N-benzyl-3-methoxypropanamide (1 g; 4.56 mmol) was dissolved in isopropyl acetate (20 mL). 2-Hydroxy-5-nitrobenzaldehyde (40 mg; 5 mol %) and (S)-2-formamido-4-methylpentanoic acid (0.76 g; 1 eq. to racemic amine) were added. The mixture was stirred at 60° C. (oil-bath) in 17 h and then allowed to cool to 25° C. Thick slurry was filtered and washed on filter with 3 mL of isopropyl acetate. 1.3 g of white solid was obtained, chiral HPLC: 92% of (R)-enantiomer and 8% of (S)-enantiomer; calculated yield of (R)-enantiomer 71% from racemic amine.

Example 3

Acetylation of (R)-2-amino-N-benzyl-3-methoxypropanamide

To a solution of (R)-2-amino-N-benzyl-3-methoxypropanamide (0.5 g; 2.38 mmol) in isopropyl acetate (5 mL) was added isopropenyl acetate (1.3 mL; 11.9 mmol). The solution was heated in oil-bath at 70-75° C. for 4 h and left then to cool to 23° C. overnight. The resulting solid was filtered and washed with isopropyl acetate (1 mL). 2-Acetamino-N-benzyl-3-methoxypropanamide (0.41 g; identity confirmed by GC-MS) with a purity of 97.2% (HPLC area %) was obtained, yield (from starting amine): 68.9%.

Example 4

Preparation of Formulations Containing Lacosamide

Lacosamide (a compound of formula III), e.g. obtained by the procedures disclosed herein, may be formulated into a pharmaceutically acceptable formulation using standard procedures.

For example, there is provided a process for preparing a pharmaceutical formulation comprising Lacosamide, or a salt thereof, which process is characterised in that it includes as a process step a process as hereinbefore defined. The skilled person will know what such pharmaceutical formulations will comprise/consist of (e.g. a mixture of active ingredient (i.e. Lacosamide or a salt thereof) and pharmaceutically acceptable excipient, adjuvant, diluent and/or carrier).

There is further provided a process for the preparation of a pharmaceutical formulation comprising Lacosamide (or a salt thereof), which process comprises bringing into association Lacosamide, or a pharmaceutically acceptable salt thereof (which may be formed by a process as hereinbefore described), with (a) pharmaceutically acceptable excipient (s), adjuvant(s), diluent(s) and/or carrier(s).

When a pharmaceutical formulation is referred to herein, it includes a formulation in an appropriate dosage form for intake (e.g. in a tablet form). Hence, any process mentioned herein that relates to a process for the preparation of a pharmaceutical formulation comprising Lacosamide, or a salt thereof, may further comprise an appropriate conversion to the appropriate dosage form (and/or appropriate packaging of the dosage form).

Example 5

Deracemisation of 2-amino-N-benzyl-3-methoxypropanamide in toluene

2-Amino-N-benzyl-3-methoxypropanamide in toluene (207 g; 12% racemic amine by NMR assay) was concentrated to 151.6 g (16.4% solution). 2-Hydroxy-5-nitrobenzaldehyde (1.1 g; 5 mol %) and (S)-2-formamido-4-methylpentanoic acid (20 g) were added. The mixture was stirred at 65-66° C. The enantiomer ratio after 45 h was 92:7 (R:S). The product was filtered and washed with toluene/isopropanol mixture. Crude wet product was re-slurried in 150 mL toluene/iPrOH (95/5) at 65-70° C. for 1 h to afford 36.8 g of (R)-salt with 99.1% purity by HPLC and undetectably low content of (S)-enantiomer. Yield of (R)-salt 84%.

Example 6

Deracemisation of 2-amino-N-benzyl-3-methoxypropanamide in a mixture of toluene and 2-propanol 2-Amino-N-benzyl-3-methoxypropanamide (10 g; 43.7 mmol) in toluene/iPrOH (88.4 g; 97/3 w/w) was mixed with (S)-2-formamido-4-methylpentanoic acid (7.02 g) and 2-hydroxy-5-nitrobenzaldehyde (0.37 g; 5 mol %). The mixture was heated in an oil-bath at 64-65° C. The enantiomer ratio was 92:7 (R:S) after 51 h. The suspension was cooled and filtered. The wet crude product (18.72 g) was re-slurried in 60 mL toluene/i-PrOH mixture (97/3 w/w) at 60-65° C. for 1 h to afford 13.85 g of (R-salt) with 98.4% purity by HPLC. Chiral purity 99.6% of (R)-enantiomer and 0.4% of (S)-enantiomer. Yield of (R)-salt 86%.

Example 7

Acetylation of the Salt of Formula I with Isopropenyl Acetate in Isopropyl Acetate The N-formyl-L-leucine salt of (R)-2-amino-N-benzyl-3-methoxypropanamide (3 g) was suspended in iPrOAc (60 mL) and isopropenyl acetate (3.5 mL; 32.1 mmol) was added. Conversion was over 99% at 85° C. in 2 h by HPLC analysis. The mixture was cooled and NaOH aqueous solution was added. The layers were separated. The organic phase was concentrated. The precipitate was filtered and washed with iPrOAc. After drying 0.8 g of white solid with 95.2% HPLC purity was achieved. From filtrate crop 2 (0.37 g) was isolated with 91.6% HPLC purity. Overall yield 55.3%.

Example 8

Acetylation of the N-formyl-L-leucine salt of (R)-2-amino-N-benzyl-3-methoxypropanamide with acetic anhydride in water The N-formyl-L-leucine salt of (R)-2-amino-N-benzyl-3-methoxypropanamide (3.0 g) was suspended in water (20 mL). The mixture was stirred at 22° C. for 40 min. Acetic anhydride (1.3 mL) was added portion-wise in 6 h at 22-25° C. The product was filtered, washed with isopropyl acetate and dried in air. White crystals (1.58 g) were obtained containing 12.4% N-formyl-L-leucine and 86.1% Lacosamide by HPLC area %.

Example 9

Acetylation of the N-formyl-L-leucine salt of (R)-2-amino-N-benzyl-3-methoxypropanamide with acetic anhydride in a mixture of water and dichloromethane The N-formyl-L-leucine salt of (R)-2-amino-N-benzyl-3-methoxypropanamide (6.0 g) was suspended in water (15 mL) and dichloromethane (25 mL). Acetic anhydride (3.4 g; 2 eq) was added at stirring in 30 min at 21 to 25° C. Stirring was continued for 1 h at 21-24° C. The mixture was neutralized with concentrated NaOH solution. The phases were separated. The water phase was extracted with dichloromethane (5 mL). The combined organic solution was washed with concentrated solution of sodium hydrogen carbonate (5 mL). The organic solution was concentrated in vacuum. Ethyl acetate (30 mL) was added to the residue and mixture was heated to reflux. The solution was stirred and cooled to 10° C. The product was filtered, washed with cold ethyl acetate and dried. Lacosamide (2.52 g) as white solid was obtained with 99.3% purity by HPLC. Yield 64%.

Example 10

Acetylation of the N-formyl-L-leucine salt of (R)-2-amino-N-benzyl-3-methoxypropanamide with acetic anhydride in a mixture of water and tert-amyl alcohol The N-formyl-L-leucine salt of (R)-2-amino-N-benzyl-3-methoxypropanamide (2.0 g) was suspended in water (5 mL) and t-amyl alcohol (10 mL). Acetic anhydride (1.1 g) was added in 20 min at 22 to 25° C. Stirring was continued for 1 h at 23-24° C. The mixture was neutralized with concentrated NaOH solution and phases were separated. The organic phase was washed with sodium hydrogen carbonate solution (4 mL). The combined water phase was extracted with t-amyl alcohol (5 mL). The organic solution was concentrated in vacuum. The solid residue (2.27 g) was heated with isopropyl acetate (15 mL) to reflux, filtered and allowed to cool to room temperature. The precipitate was filtered off, washed with isopropyl acetate and dried. Lacosamide (0.95 g) as white solid was obtained with 98.9% Lacosamide purity by HPLC area %. Yield 73%.

Example 11

Preparation of (R,S)-methyl 2-chloro-3-methoxypropionate

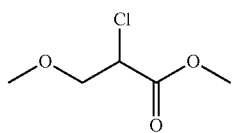

NaOMe (30% in MeOH, 120.3 g; 0.669 mol) was diluted with MeOH (120 g; 154 mL) to reach 15% w/w concentration of NaOMe in MeOH. The resulting solution was cooled to 0±5° C. and then methyl-2,3-dichloropropionate (100.1 g; 0.637 mol) was added at 5° C. The reaction mixture was stirred at 0±5° C. for 2 h, after which the excess NaOMe was neutralized by alcoholic HCl solution (4.6 mL, 20% in i.PrOH) until pH 5-6 was reached. The precipitate was filtered off and the cake washed with cold MeOH (100 mL). Excess MeOH was removed by distillation at atmospheric pressure. The product was purified by distillation in vacuo to obtain methyl 2-chloro-3-methoxypropionate (81.8 g, 0.533 mol, >99 GC area %, yield 83.6%).

Example 12

Preparation of (R,S)-methyl 2-bromo-3-methoxypropionate

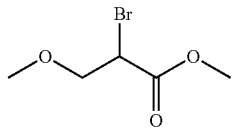

Methyl acrylate (151.8 g; 1.76 mol) was dissolved in MTBE (400 ml). Bromine (308.4 g; 1.92 mol; 100 mL) was added dropwise to the resulting solution at 18-25° C. The mixture was allowed to stir for 18 h at room temperature. Excess bromine was quenched with ca. 30% sodium sulfite solution (100 mL). The brownish organic phase became colourless after vigorous stirring. The layers were separated and the organic phase was concentrated in vacuo. The crude methyl 2,3-dibromopropionate (524.7 g; 91% pure by GC area %) was then added dropwise at 18-20° C. into a sodium methoxide solution prepared from sodium methoxide (317.5 g; 1.76 mol) and methanol (634.0 g; 810 mL). The resulting mixture was allowed to stir for 15 min at room temperature. GC analysis revealed: Br-acrylate 1.5%; methyl 2-bromo-3-methoxypropionate 96% by area %. Methanol was removed by distillation in vacuo. Toluene (200 mL) was added and the mixture was concentrated again. The resulting precipitate was filtered off and the filtrate was distilled in vacuo. A product fraction was collected at 32 mbar and 92-93° C., affording methyl 2-bromo-3-methoxypropionate (251.8 g, 1.28 mol, 96 GC area %, yield 70% based on methyl acrylate).

Example 13

Preparation of (R,S)—N-Benzyl-2-benzylamino-3-methoxypropionamide

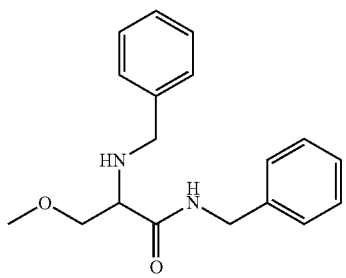 [SMILES: COCC(NCc1ccccc1)C(=O)NCc1ccccc1]

Methyl 2-chloro-3-methoxypropionate (3.70 kg, 24.2 mol) was added to benzylamine (13.50 kg, 126 mol) over 30 min. The mixture was stirred at 120±5° C. for 6 h, while the resulting MeOH was collected as a distillate. After cooling the reaction mixture below 100° C., water (4.35 kg) and NaOH (89% by titration, 1.22 kg, 27.27 mol, 1.13 eq.) were added and the resulting two phase system was thoroughly mixed and allowed to settle before the phases were separated. Aqueous NaCl (ca. 20%, 2.65 kg) was added to the organic phase, the mixture was allowed to settle and the layers were separated to remove excess NaOH. The process was repeated until pH 10-11 was obtained. The organic phase was dried by distillation at 100-150 mbar and 56-87° C. which produced a small amount of solid precipitated. The residue was filtered off, the cake was washed with benzylamine (100 mL) and the filtrate subjected to further distillation to remove benzylamine (6.99 kg). The residue from the distillation was collected (7.00 kg, 22.03 mol, assay 93.7% by NMR, yield 89.9%).

Example 14

Preparation of (R,S)—N-Benzyl-2-benzylamino-3-methoxypropionamide

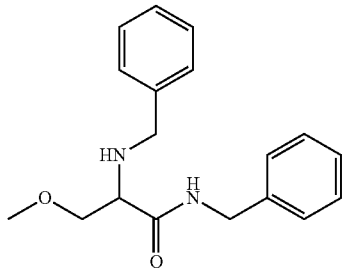 [SMILES: COCC(NCc1ccccc1)C(=O)NCc1ccccc1]

NaOMe (25% in MeOH, 46 g; 0.213 mol) was diluted with MeOH (100 g; 128 mL). The resulting solution was cooled to 0±5° C. and then methyl 2,3-dichloropropionate (32 g; 0.204 mol) was added at 5° C. The reaction mixture was stirred at 0±5° C. for 2 h after which, the excess NaOMe was neutralized by alcoholic HCl solution until pH 6-7 was reached. Benzylamine (88 g; 0.82 mol) was added to the mother liquor, and the mixture was heated to 125±5° C. while methanol was removed via distillation. After 12 h the mixture was cooled and isopropyl acetate (180 mL) and water (100 mL) were added. The aqueous phase was separated and removed, and the organic phase was washed with aqueous acetic acid (16%, 60 mL) and then with water (3×50 mL). The solvent was partially distilled off to remove water to obtain about 58 g of an oil, containing 48.6 g of (R,S)—N-benzyl-2-benzylamino-3-methoxypropionamide (0.163 mol, yield 80%) which was used in the next step without any isolation or further purification.

Example 15

Preparation of (R,S)—N-Benzyl-2-amino-3-methoxypropionamide [(R,S)-II]

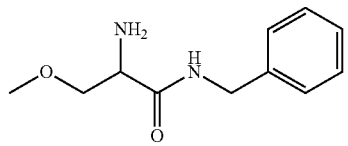

N-Benzyl-2-benzylamino-3-methoxypropanamide (400 g, 94%, 1.26 mol), toluene (400 g) and a catalyst (5% Pd/C, 50% moist, 21.5 g, 0.4 mol %) were sequentially introduced into a pressure reactor. The atmosphere in the reactor was exchanged to $N_2$ and then to $H_2$. The reaction mixture was stirred at 100° C. and 2.0 to 2.5 bar for 4 h and then cooled to 22° C., after which the catalyst was filtered off and the cake washed with toluene (60 mL). The toluene solutions were combined to give a toluene solution of (R,S)—N-benzyl-2-amino-3-methoxypropionamide (798.7 g, HPLC purity 94.7%, yield 94.5%).

Example 16a

Preparation of (R,S)—N-Benzyl-2-amino-3-methoxypropionamide

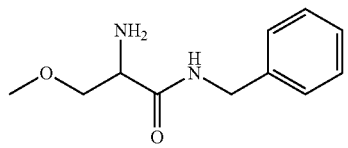

An oil (58 g; prepared according to Example 14) containing 48.6 g of (R,S)—N-benzyl-2-benzylamino-3-methoxypropionamide (0.163 mol) was placed in a pressure reactor and diluted with isopropyl acetate (600 mL). A catalyst (5% Pd/C, 50% moist, 2.9 g, 5% w/w) was added to this solution and the atmosphere in the reactor was exchanged to $N_2$ and then to $H_2$. The reaction mixture was stirred at 85° C. and 2.0 bar for about 12 h and then cooled to 22° C., after which the catalyst was filtered off and the cake washed with isopropyl acetate (50 mL) to give (R,S)—N-benzyl-2-amino-3-methoxypropionamide as an isopropyl acetate solution (36 g, HPLC purity 90%, corresponding to 32.4 g of (R,S)—N-benzyl-2-amino-3-methoxypropionamide (0.156 mol), yield 95%, in 650 mL of isopropyl acetate).

Example 16b

Preparation of (R,S)—N-Benzyl-2-amino-3-methoxypropionamide

The procedure of Example 16a was reproduced using 300 mL of isopropyl acetate in the initial stage. The final product was an isopropyl acetate solution of (R,S)—N-benzyl-2-amino-3-methoxypropionamide which was obtained in a similar yield with a similar purity (as determined by HPLC).

Example 17

Preparation of (R)—N-benzyl-2-amino-3-methoxypropanamide N-formyl-L-leucine salt

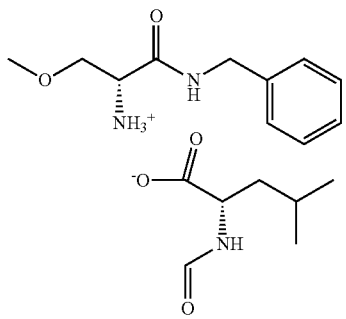

An isopropyl acetate solution of (R,S)—N-Benzyl-2-amino-3-methoxypropionamide (36 g, 90% pure in 650 mL of solvent; prepared according to Example 16a), was added to N-formyl-L-leucine (24.8 g, 0.156 mol), 5-nitro-salicylic aldehyde (1.25 g, 7.4 mmol), and isopropanol (35 mL), and the mixture was stirred at 65° C. for about 16 h. The mixture was then cooled at room temperature and filtered. The cake was washed with isopropyl acetate/isopropanol (90/10, 2×20 mL) to give (R)—N-benzyl-2-amino-3-methoxypropanamide N-formyl-L-leucine salt (48 g, 0.131 mol, HPLC purity >99%, d.e. ≥99%, yield 84%).

Example 18a

Preparation of (R,S)—N-benzyl-2-amino-3-methoxypropanamide from the corresponding (S) enantiomer

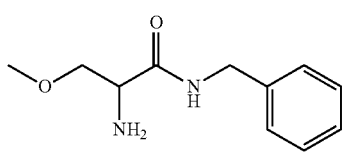

A solution containing toluene (90 mL) and enriched (S)—N-benzyl-2-amino-3-methoxypropanamide (13 g, 62 mmol, e.e. 80%) was treated with 5-nitro-salicylic aldehyde (0.5 g, 3.0 mmol) and heated at 65° C. for 16 h to afford (R,S)—N-benzyl-2-amino-3-methoxypropanamide quantitatively.

Example 18b

Preparation of (R,S)—N-benzyl-2-amino-3-methoxypropanamide from the corresponding (S) enantiomer A solution containing toluene (90 mL) and enriched (S)—N-benzyl-2-amino-3-methoxypropanamide (13 g, 62 mmol, e.e. 80%) was treated with a mixture containing salicylic aldehyde (0.5 g, 4.0 mmol), potassium carbonate (0.2 g, 1.4 mmol), and tetrabutylammonium bromide (0.1 g, 0.3 mmol), and heated at 65° C. for 16 h to afford (R,S)—N-benzyl-2-amino-3-methoxypropanamide (e.e. for (S)-enantiomer: 10%).

Example 19

(R)—N-benzyl-2-acetamido-3-methoxypropanamide (Lacosamide)

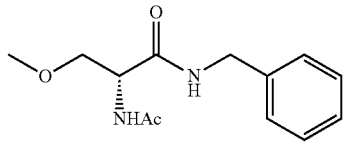 [SMILES: COC[C@@H](NC(C)=O)C(=O)NCc1ccccc1]

Acetic anhydride (12 g, 0.117 mol) was added to a mixture of (R)—N-benzyl-2-amino-3-methoxypropanamide N-formyl-L-leucine salt (40 g, 0.109 mol, d.e. ≥99%), isopropyl acetate (180 mL), water (25 mL) and anhydrous sodium acetate (9.5 g, 0.116 mol) at room temperature. After about 2 h, the mixture was treated with sodium hydroxide (30%) to reach pH 6-7 and heated to obtain two clear phases. The aqueous phase was separated and extracted with isopropyl acetate (3×15 mL). The organic phases were brought together and washed with an aqueous solution of potassium bicarbonate (20%, 15 mL). The organic phase was then distilled off in a Dean-Stark equipment to reduce the water content of the organic phase (to K.F. <0.5). After the product was slowly cooled to 0 to 5° C., the product was filtered, washed with cold isopropyl acetate (2×15 mL) and dried to obtain (R)—N-benzyl-2-acetamido-3-methoxypropanamide (23.2 g, 92.6 mmol, HPLC purity >99%, d.e. ≥99%, yield 85%).

Example 20

Recovery of N-Formyl-L-Leucine

The aqueous phase obtained during the process of Example 19 was treated with 32% aqueous HCl to reach pH 2-3. The resulting slurry was stirred for about 1 h at 20-25° C., then filtered and washed with water (3×20 mL) to obtain N-formyl-L-leucine as a white solid (13.8 g, yield 80%). This product may be used as such for a new preparation of (R)—N-benzyl-2-amino-3-methoxypropanamide N-formyl-L-leucine salt, for example according to the procedure of Example 17.

Example 21

Crystallization of Lacosamide

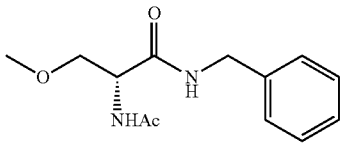 [SMILES: COC[C@@H](NC(C)=O)C(=O)NCc1ccccc1]

Lacosamide (20 g; obtained according to Example 19) were placed in a round bottom flask equipped with mechanical stirrer. Wet isopropyl acetate (180 mL) was added (Karl Fisher value of the solvent was 1.3-1.5%). The mixture was heated at reflux (complete solution at 70° C.). The solution was filtered while hot on paper and the filter was washed with hot wet isopropyl acetate (10 mL). The solution was distilled off in a Dean-Stark apparatus to remove water (the final KF of the solution was <0.1%; the temperature of reflux raised from 82 to 86° C.). The resulting solution was cooled until a solid formed (at approximately 60 to 65° C.) and heated again up to 70 to 75° C. without total dissolution occurring. The resulting suspension was maintained at this temperature for 1 hour. The suspension was then cooled to room temperature over 2 hours and finally to 0 to 5° C. over one hour. The suspension was maintained at 0 to 5° C. for another hour. The solid was obtained by filtration at this temperature and the filter was rinsed with 20 mL of cold anhydrous isopropyl acetate. 24.7 g of wet product was obtained (corresponding to 18.4 g of dry product after drying at 65° C. under vacuum).

The solid form of Lacosamide obtained here was characterized by X-ray Powder Diffraction (XRDP) using a Philips PW1800/10 diffractometer, equipped with software X'Pert High Score—v. 2.0a (PANalytical) and radiation Cu Kα. The peak intensities recorded are shown in Table 1.

TABLE 1

XRPD data for Lacosamide

| Pos. [° 2θ] | d-spacing [Å] | Rel. Int. [%] |
|---|---|---|
| 6.5369 | 13.52180 | 1.86 |
| 8.3517 | 10.58717 | 55.99 |
| 10.4373 | 8.47587 | 7.84 |
| 13.0610 | 6.77854 | 98.21 |
| 15.6497 | 5.66262 | 17.05 |
| 16.6567 | 5.32246 | 22.31 |
| 17.7101 | 5.00820 | 8.83 |
| 19.6494 | 4.51807 | 24.04 |
| 20.8974 | 4.25098 | 59.96 |
| 21.4595 | 4.14089 | 51.50 |
| 22.6569 | 3.92469 | 4.05 |
| 24.0023 | 3.70765 | 23.49 |
| 24.2687 | 3.66756 | 30.93 |
| 24.9861 | 3.56385 | 100.00 |
| 25.4293 | 3.50274 | 48.18 |
| 26.1188 | 3.41181 | 15.02 |
| 27.0174 | 3.30035 | 11.09 |
| 28.0044 | 3.18622 | 10.23 |
| 28.4115 | 3.14149 | 9.93 |
| 31.5304 | 2.83750 | 9.57 |
| 32.1197 | 2.78677 | 8.28 |
| 33.6009 | 2.66724 | 13.54 |
| 34.0918 | 2.62995 | 4.63 |
| 36.4979 | 2.46191 | 6.13 |
| 37.4792 | 2.39968 | 4.97 |
| 38.5423 | 2.33589 | 9.37 |
| 38.9474 | 2.31253 | 7.16 |
| 40.4187 | 2.23168 | 9.78 |
| 41.1488 | 2.19376 | 8.72 |
| 43.9879 | 2.05853 | 4.30 |
| 45.0527 | 2.01232 | 3.97 |
| 45.9179 | 1.97640 | 5.87 |
| 47.0455 | 1.93163 | 7.38 |
| 47.7339 | 1.90536 | 5.13 |
| 51.2066 | 1.78401 | 2.68 |
| 53.8756 | 1.70176 | 1.02 |
| 57.3169 | 1.60750 | 1.22 |
| 61.8188 | 1.49956 | 0.79 |

FT-IR spectra were recorded using a Jasco FT/IR 460 plus spectrometer. The spectra were recorded using the diffuse reflection method and the sample was prepared mixing about 5 mg of product with 500 mg of KBr (10% w/w).

Absorptions were observed at ca.: 3300, 3100, 2880, 1630, 1550, 1140, 970, 690, 600 and 500 $cm^{-1}$.

DSC data was collected using a Mettler-Toledo DSC 822e instrument. Standard DSC experiment: heat 30-250° C. at 10°/min.

A single transition was observed with the following results:

Onset 145.52° C.

Peak 146.54° C.

Endset 149.13° C.

ABBREVIATIONS

DCM dichloromethane d.e. diastereomeric excess

DMAA N,N-dimethylacetamide

DMAP dimethylaminopyridine

DMF dimethylformamide

DSC Differential scanning calorimetry e.e. enantiomeric excess

GC gas chromatography h hours

HPLC high performance liquid chromatography iPrOAc isopropyl acetate iPrOH isopropyl alcohol IR Infrared KF Karl Fischer MeOH methanol MTBE methyl-tert-butyl ether NMP N-methylpyrrolidone NMR Nuclear magnetic resonance RA racemic 2-amino-N-benzyl-3-methoxypropionamide RT room temperature TEA triethylamine THF tetrahydrofuran TMEDA tetramethylethylenediamine XRPD X-ray powder diffraction

The invention claimed is:

1. A salt of formula I,

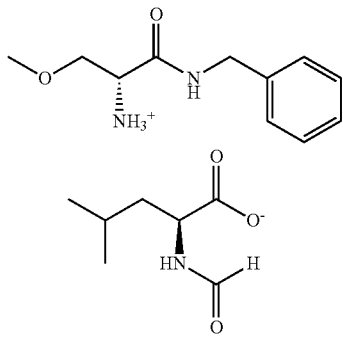

or a solvate thereof.

2. The salt according to claim 1 having a percentage diastereomeric excess of greater than 90%.

3. A process for the isolation of salt of formula I,

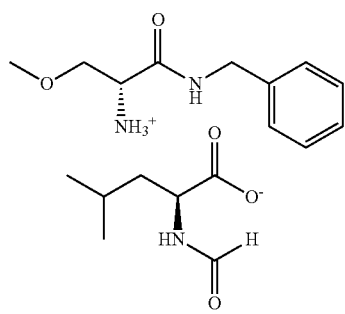

which process comprises precipitation of the salt of formula I from a mixture of N-formyl-L-leucine, a compound of formula II,

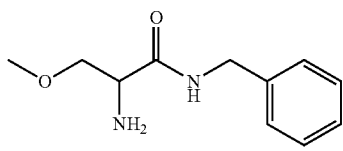

and a solvent for the compound of formula II.

4. The process according to claim 3, wherein the N-formyl-L-leucine has a percentage enantiomeric excess of the L-enantiomer of greater than 95%.

5. The process according to claim 3, wherein the process comprises the addition of N-formyl-L-leucine to a mixture of a compound of formula II and a solvent for the compound of formula II.

6. The process according to claim 3, wherein the process is performed in the presence of a racemisation promoter.

7. The process according to claim 6, wherein the racemisation promoter is selected from 5-nitrosalicylic aldehyde, 3,5-dichlorosalicylic aldehyde, 2-nitro benzaldehyde, 4-nitrobenzaldehyde, 2,4-dinitrobenzaldehyde, salicylic aldehyde and pyridoxal-5'-phosphate.

8. The process according to claim 7, wherein the racemisation promoter is present at about 2 to about 20 mol % relative to the compound of formula II.

9. The process according to claim 3, wherein the solvent for the compound of formula II is one or more organic solvents selected from the group consisting of toluene, a xylene, ethylbenzene, an alkylbenzene, a halobenzene, a nitrobenzene, a methoxybenzene, 2-propanol, methylcyclohexane, a heptane, an alkenyl acetate and an alkyl acetate.

10. The process according to claim 9, wherein the solvent for the compound of formula II is isopropyl acetate, toluene or a mixture of isopropyl acetate and isopropanol.

11. The process according to claim 3, wherein the process is conducted at a temperature from about 30° C. to about 80° C.

12. A process for preparing a compound of formula IIA,

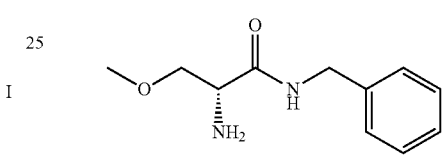

said process comprising the steps of
isolating, by precipitation, a salt of formula I

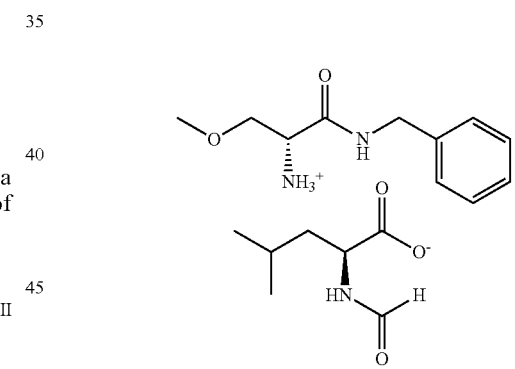

from a mixture of N-formyl-L-leucine. a compound of formula II, and a solvent for the compound of formula II,
and reacting the salt of formula I with a base.

13. A process for the preparation of Lacosamide (formula III):

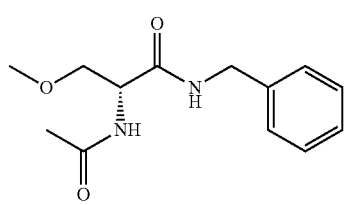

which process comprises:
isolating a salt of formula I,

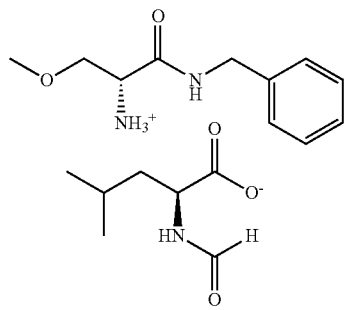

by precipitation of the salt of formula I from a mixture of N-formyl-L-leucine, a compound of formula II,

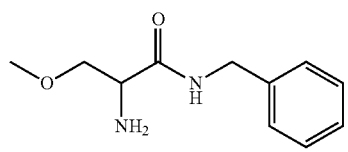

and a solvent for the compound of formula II, followed by reaction of the salt of formula I with an acetyl donor optionally in the presence of a base.

14. The process according to claim 13, wherein the acetyl donor is a branched or linear $C_{2-8}$ 1-alkenyl acetate.

15. The process according to claim 14, wherein the acetyl donor is isopropenyl acetate.

16. The process according to claim 13, wherein the acetyl donor is acetic anhydride.

17. The process of claim 13 wherein the Lacosamide is then crystallized in a suitable solvent to yield a polymorph of Lacosamide having an X-ray powder diffraction pattern containing specific peaks of high intensity at 8.4° (±0.1°), 13.1° (±0.1°), 20.9° (±0.1°), 21.5° (±0.1°), 25.0° (±0.1°) and 25.4° (±0.1°) 2θ.

18. The process of claim 17 wherein the compound of formula II is prepared by a process which comprises the following steps:
(a) reacting a compound of formula IX,

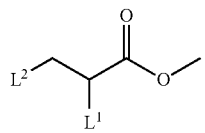

wherein $L^1$ and $L^2$ independently represent a halogen atom, to produce a compound of formula IV,

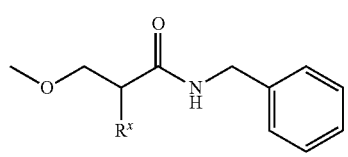

wherein $R^x$ represents a NH-benzyl group; and (b) reducing the compound of formula IV obtained in step (a) to produce the compound of formula II

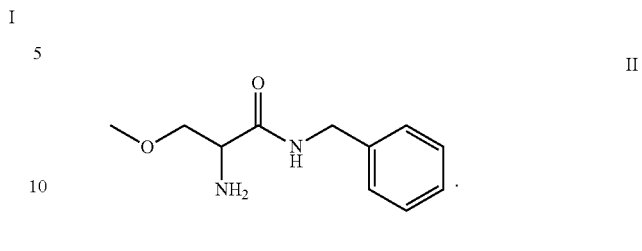

19. The process of claim 18 further comprising preparing a pharmaceutical formulation by admixing the Lacosamide with one or more pharmaceutically acceptable adjuvants, diluents and/or carders and, optionally, one or more other pharmacologically active agents.

20. A process for the preparation of Lacosamide (formula III):

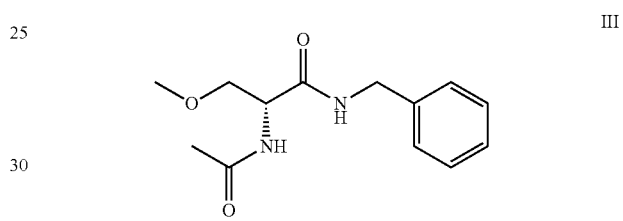

which process comprises isolating a salt of formula I,

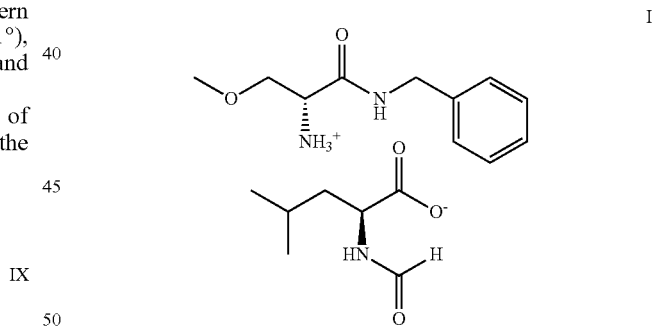

by precipitating the salt from a mixture of N-formyl-L-leucine, a compound of formula II,

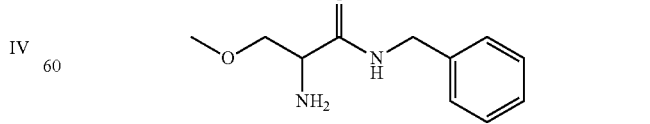

and a solvent for the compound of formula II:
reacting the salt of formula I with a base to produce a compound of formula IIA,

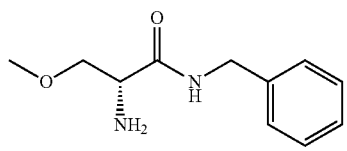

IIA followed by reaction of the compound of formula IIA with an acetyl donor.

21. The process according to claim 20, wherein the acetyl donor is a branched or linear $C_{2-8}$ 1-alkenyl acetate.

22. The process according to claim 21, wherein the acetyl donor is isopropenyl acetate.

23. The process according to claim 20, wherein the acetyl donor is acetic anhydride.

24. The process of claim 20 wherein the Lacosamide is then crystallized in a suitable solvent to yield a polymorph of Lacosamide having an X-ray powder diffraction pattern containing specific peaks of high intensity at 8.4° (±0.1°), 13.1° (±0.1°), 20.9° (±0.1°), 21.5° (±0.1°), 25.0° (±0.1°) and 25.4° (±0.1°) 2θ.

* * * * *